United States Patent
Shih et al.

(10) Patent No.: US 7,638,656 B2
(45) Date of Patent: Dec. 29, 2009

(54) HYDROFORMYLATION PROCESS

(75) Inventors: Kuo-Chen Shih, Kaohsiung (TW); Mao-Lin Hsueh, Pingtung County (TW); Hao-Hsun Yang, Tainan (TW)

(73) Assignee: Industrial Technology Research Institute, Hsinchu County (TW)

( * ) Notice: Subject to any disclaimer, the term of this patent is extended or adjusted under 35 U.S.C. 154(b) by 0 days.

(21) Appl. No.: 12/276,335

(22) Filed: Nov. 22, 2008

(65) Prior Publication Data
US 2009/0171125 A1 Jul. 2, 2009

(30) Foreign Application Priority Data
Dec. 31, 2007 (TW) ................ 96151426 A

(51) Int. Cl.
*C07C 45/50* (2006.01)
(52) U.S. Cl. ..................................... 568/444
(58) Field of Classification Search .................. 568/451, 568/454
See application file for complete search history.

(56) References Cited

U.S. PATENT DOCUMENTS

| 4,262,147 | A | 4/1981 | Garrou et al. |
| 4,300,002 | A | 11/1981 | Shibatani et al. |
| 6,365,782 | B1 | 4/2002 | Nakamura et al. |
| 6,939,997 | B2 | 9/2005 | Lappe et al. |
| 7,015,362 | B2 | 3/2006 | Lappe et al. |
| 7,087,797 | B2 | 8/2006 | Sielcken et al. |
| 7,122,706 | B2 | 10/2006 | Lappe et al. |
| 2005/0101805 | A1 | 5/2005 | Lappe et al. |
| 2005/0107640 | A1 | 5/2005 | Lappe et al. |
| 2005/0107644 | A1 | 5/2005 | Lappe et al. |
| 2005/0272960 | A1 | 12/2005 | Dukat et al. |
| 2007/0100168 | A1 | 5/2007 | Papp et al. |

FOREIGN PATENT DOCUMENTS

| JP | 1981-030938 A | 3/1981 |
| JP | 1988-119429 A | 5/1988 |
| JP | 1999-080067 A | 3/1999 |
| JP | 1999-100339 A | 4/1999 |
| JP | 2000-143573 A | 5/2000 |
| JP | 2001-010999 A | 1/2001 |
| JP | 2003-146931 A | 5/2003 |
| WO | 9302024 A2 | 2/1993 |

*Primary Examiner*—Sikarl A Witherspoon
(74) *Attorney, Agent, or Firm*—Pai Patent & Trademark Law Firm; Chao-Chang David Pai

(57) ABSTRACT

The disclosed is about a hydroformylation reaction of a cyclic olefin in the presence of a rhodium catalyst, and specifically about recovering the rhodium catalyst. After the cyclic olefin is hydroformylated by the rhodium catalyst, the product solution is added an extraction liquid including a cycloalkyl alcohol and separated into two layers. The upper layer is substantially made up of the rhodium catalyst solution, and the lower layer is substantially made up of the cycloalkyl aldehyde and the extraction solution including cycloalkyl alcohol.

14 Claims, No Drawings

HYDROFORMYLATION PROCESS

BACKGROUND OF THE INVENTION

1. Field of the Invention

The present invention relates to a hydroformylation process of cyclic olefins in the presence of a metal catalyst, and in particular relates to the separation of the desired products from the metal catalyst by phase separation.

2. Description of the Related Art

It is known in the art that compared to a heterogeneous catalyst, the homogeneous catalyst has advantages such as high reactivity, high selectivity, and a relatively milder reaction condition. However, many homogeneous catalyst systems cannot be commercially applied mainly due to difficulties in separating, recovering, and reusing the homogeneous catalysts, as it is well known.

It is known in the art that distillation is one of the favorable methods for the separation of catalysts and products. If the volatility of the product is low, the temperature required to separate the product by distillation should be higher. Most homogeneous catalysts, however, are thermal sensitive, such that the homogeneous catalyst may decompose during higher distillation temperatures and fail to be recovered for reuse. Other methods for recovering the homogeneous catalyst, e.g. chromatography, are inefficient. Accordingly, an effective and low cost separation process is critical for development of the homogeneous catalyst.

Hydroformylation of olefins with carbon monoxide (hereinafter CO) and hydrogen (hereinafter $H_2$) to form aldehydes is an important homogeneous catalytic reaction. The catalysts used for the hydroformylation of olefins are usually rhodium or cobalt catalysts, especially the rhodium catalysts due to their high reactivity and selectivity. Although rhodium catalysts have higher reactivity, their cost is much higher than the cobalt catalysts. The effective recovery and reuse of the rhodium catalysts determines their realization in the industry. If the volatility of the hydroformylation products (less than C5) is relatively high, the low temperature distillation method can be used to separate the products and the catalysts without significantly decomposing the catalysts. On the other hand, if the volatility of the hydroformylation products is low, the abovementioned distillation method for separation is unfavorable, due to the decomposition of the catalyst at higher temperatures such that the catalyst cannot be recovered and reused, thus increasing costs.

As described above, the products from hydroformylation of cyclic olefins have a higher boiling point. If the product and catalyst are separated by vacuum distillation, a higher distillation temperature is needed, thereby decomposing the rhodium catalyst. In WO 93/02024, a mixture of first alcohol having 1 to 3 carbon atoms and water is reported to be used as an extraction solution to separate the rhodium catalyst and high boiling-point aldehydes from hydroformylation. The efficiency of this method is, however, not good, and a better method for the efficient separation of the hydroformylation products and catalyst is still needed.

BRIEF SUMMARY OF THE INVENTION

The invention provides a hydroformylation process, comprising: (i) Reacting a cyclic olefin compound with carbon monoxide and hydrogen in a solvent in the presence of a metal-organophosphorus ligand complex catalyst, optionally free organophosphorus ligand to obtain a hydroformylation product liquid containing cycloalkyl aldehydes; (ii) Mixing the hydroformylation product liquid with an extraction liquid comprising a first cycloalkyl alcohol, and allowing the resultant mixture to separate into a first layer and a second layer, wherein a substantial part of the first layer comprises the metal-organophosphorus ligand complex catalyst and a substantial part of the second layer comprises the first cycloalkyl alcohol and the cycloalkyl aldehydes; and (iii) Separating the first layer from the second layer.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a hydroformylation process. First, a rhodium compound and an organophosphorus compound are mixed in an appropriate solvent. The rhodium compound includes rhodium trichloride hydrate ($RhCl_3 \cdot xH_2O$), dicarbonyl acetylacetone rhodium ($Rh(acac)(CO)_2$), bis(dicarbonyl chloro rhodium (($RhCl(CO)_2)_2$), carbonyl rhodium ($Rh_6(CO)_{16}$ or $Rh_4(CO)_{12}$), rhodium (III) nitrate ($Rh(NO_3)_3$), and the likes. The rhodium catalyst solution has a concentration of 10 ppm to 1000 ppm, and preferably 100 ppm to 600 ppm. The organophosphorus compound can be any phosphorus-containing organics, such as tris(2,4-di-tert-butylphenyl) phosphite, triphenylphosphite, tris(3-methyl-6-tert-butylphenyl) phosphite, tris(2,4-di-tert-butylphenyl) phosphate, di(2-tert-butylphenyl)-tert-butylphosphite, trialkyl phosphine or other suitable phosphorus-containing organics. The rhodium compound and the organophosphorus compound have a molar ratio of 1:1 to 1:300, and preferably 1:10 to 1:150. The solvent used for the catalytic reactions can be alkane, cycloalkane, or other solvent with low polarity. In one embodiment, the solvent is methyl cyclohexane.

The described rhodium catalyst solution is charged in a high pressure reaction vessel, and then added a cyclic olefin to undergo a hydroformylation reaction under high pressure of $H_2$ and CO to obtain the cycloalkyl aldehyde product. The molar ratio of $H_2$ and CO in this reaction is 1:10 to 10:1, and preferably 1:3 to 3:1. The reaction temperature is at 40° C. to 160° C., and preferably 70° C. to 140° C. The pressure of the $H_2$ and CO is between 0.5 MPa and 15 MPa, and preferably 2 MPa to 10 MPa. The cyclic olefin may have one carbon-carbon double bond or multiple carbon-carbon double bonds, such as dicyclopentadiene (hereinafter DCPD), tricyclopentadiene (hereinafter TCPD), dicyclohexadiene (hereinafter DCHD), cyclohexene, cyclohexene-1-carbaldehyde, (abbreviated CHCA), 1,2,3,6-tetrahydrobenzaldehyde, or other cyclic olefin such as methyl-3-cyclohexene-1-carboxaldehyde, methyl-4-cyclohexene-2-carboxaldehyde, 3-cyclohexene-1-carbonitrile, 3-cyclohexene-1-methanol, methyl 3-cyclohexene-1-carboxylate, 3-cyclohexene-1-carboxylate, 4-acetyl-1-cyclohexene, 1-methyl-4-cyclohexene-2-carboxylate, 1-phenyl-4-cyclohexene-2-carboxaldehyde, 1,2,3,6-tetrahydrophthalic anhydride.

The cycloalkyl aldehydes formed from cyclic olefins such as DCPD, TCPD, DCHD, cyclohexene, CHCA by hydroformylation reactions are shown in Formulae 1-8.

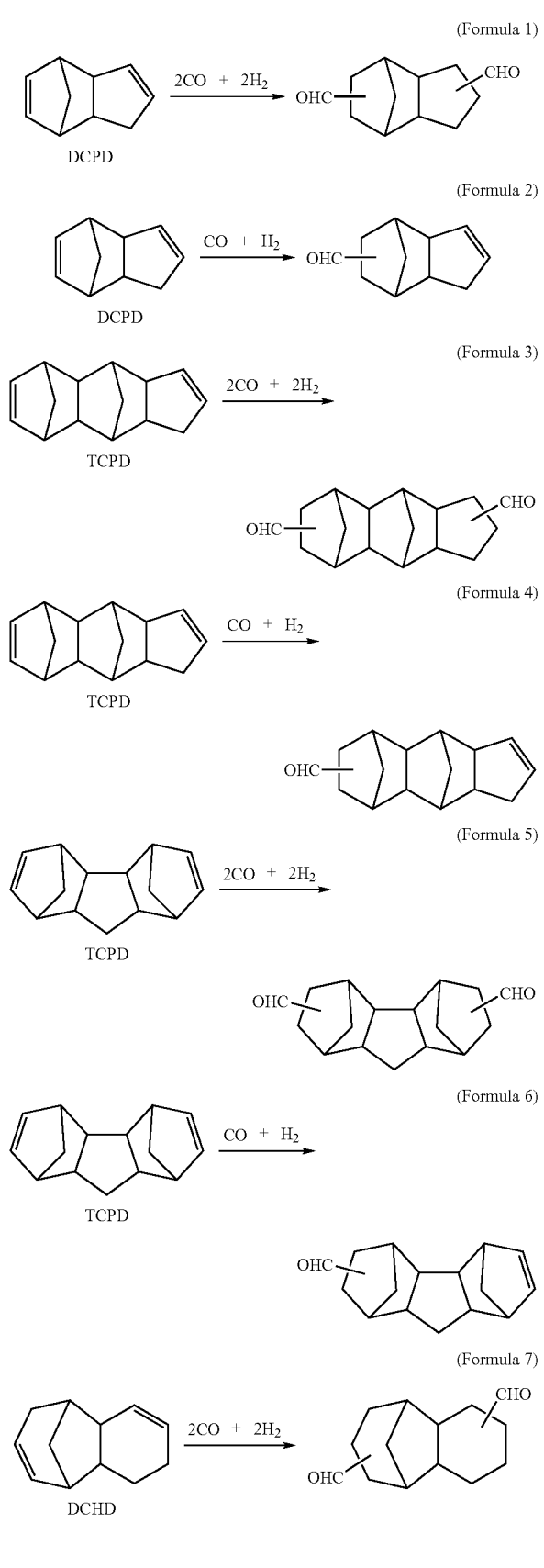

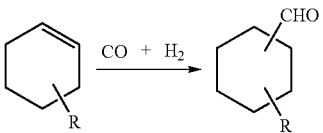

The R in Formula 8 can be hydrogen or a substituent selected from alkyl, alcohol, aldehyde, carboxylic acid, or other functional groups.

After the hydroformylation reaction process, the resulting hydroformylation product liquid was mixed with an extraction liquid including a cycloalkyl alcohol. Subsequently, the mixture was divided into two layers. One layer was substantially of the rhodium catalyst, and another layer was substantially of the extraction liquid and the cycloalkyl aldehyde product. The described two layers were separated to complete the so-called separation of the cycloalkyl aldehyde and the rhodium catalyst solution. Note that the cycloalkyl alcohol of the extraction liquid may have one or multiple alcohol functional groups.

The separated rhodium catalyst solution can be added another cyclic olefin to undergo another hydroformylation reaction. The separation method described recovers and reuses the rhodium catalyst, and efficiently separates the rhodium catalyst solution and the cycloalkyl aldehyde with high boiling point. The cycloalkyl aldehyde dissolved in the extraction liquid including the cycloalkyl alcohol, can be further hydrogenated under high pressure of $H_2$. This hydrogenation reaction can be carried out at 40° C. to 200° C., and preferably 60° C. to 180° C. The pressure of $H_2$ for the reaction is from 0.1 MPa to 10 MPa, and preferably from 1 MPa to 10 MPa. The metal catalyst used for the hydrogenation reaction can be nickel, cobalt, ruthenium, palladium, rhodium, platinum, copper chromium alloy, copper zinc alloy, and the likes. After the described hydrogenation reaction, the corresponding cycloalkyl alcohols are formed from the cycloalkyl aldehydes dissolved in the extraction liquid. In one embodiment, the hydrogenation product cycloalkyl alcohol serves as the extraction liquid to separate the rhodium catalyst and the product cycloalkyl aldehyde during the hydroformylation reaction process. Because the extraction liquid and the hydrogenation product are similar, the additional separation step of the extraction liquid and the cycloalkyl aldehyde before subsequent hydrogenation can be eliminated. The cycloalkyl alcohols formed from cycloalkyl aldehydes through the hydrogenation reaction are shown in Formulae 9 to 15.

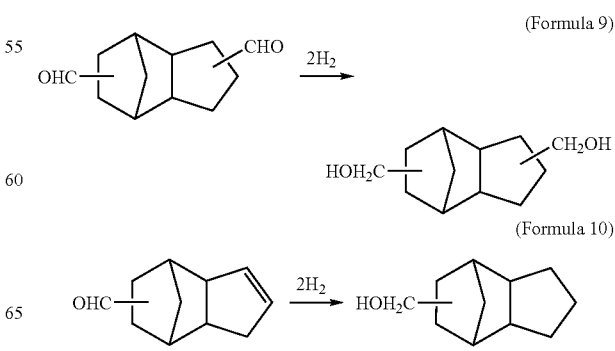

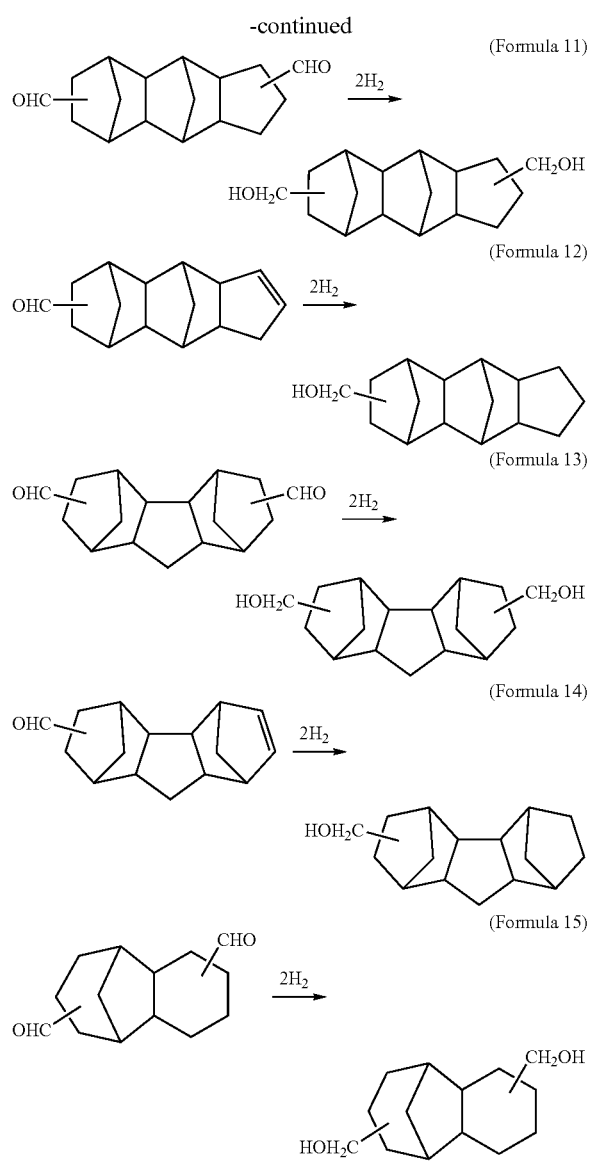

EXAMPLES

Example 1

Rh(acac)(CO)$_2$ (114 mg; 0.435 mmol) and tris(2,4-di-tert-butylphenyl)phosphite (5.625 g; 8.7 mmol) were added into a flask, followed by the addition of dry methylcyclohexane (26 g) in the dry box. A high pressure reaction vessel was heated to 80° C., followed by vacuum and recharging with nitrogen for three times, and cooled to room temperature. The rhodium solution was transferred to the high pressure reaction vessel, and the nitrogen in the high pressure reaction vessel was replaced with a mixture of CO/H$_2$(1:1). The pressure inside the vessel was built-up to 40 atm, the reaction vessel was heated to 100° C., and the pressure was then built to 50 atm.

DCPD (40 g; Fluka) and dry methylcyclohexane (4 g) were weighted and charged into a feeding bottle. The DCPD was then fed into the high pressure reaction vessel (20 mL/hours) from the feeding bottle with a feeding time of about 2 hours. The total pressure of the CO/H$_2$ was maintained at 50 atm, and the reaction temperature was also maintained at 100±2° C. throughout the reaction. Two hours after the completion of the DCPD feeding, the reaction vessel was cooled to room temperature, and the pressure of the reaction vessel was decreased to the atmospheric pressure. The cycloalkyl alcohol of Formula 9 was then added to the reaction product fluid to be divided into two layers. The layers were separated and then analyzed by a gas chromatograph (GC) and an inductively coupled plasma mass spectrometry (ICP-MS). According to the GC data, the cycloalkyl aldehyde had a yield of 99% and a partition coefficient between the upper and lower layer layers of 15.3. According to the ICP-MS data, the partition coefficient of the rhodium catalyst between the upper and lower layers was 18.5.

The lower layer, substantially of cycloalkyl aldehyde and cycloalkyl alcohol of Formula 9, was added THF (100 g), added ruthenium catalyst (6 g; 5 wt % Ru/C; Aldrich), and reacted under 1 MPa H$_2$ at 120° C. for 2 hours to hydrogenate the cycloalkyl aldehyde to obtain a corresponding cycloalkyl alcohol. According to the GC analysis, the product cycloalkyl alcohol had a yield greater than 99%.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A hydroformylation process, comprising:
   (i) reacting a cyclic olefin with carbon monoxide and hydrogen in a solvent in the presence of a metal-organophosphorus complex, optionally free organophosphorus ligand to obtain a hydroformylation product liquid containing cycloalkyl aldehydes;
   (ii) mixing the hydroformylation product liquid with an extraction liquid comprising a first cycloalkyl alcohol, and allowing the resultant mixture to separate into a first layer and a second layer, wherein a substantial part of the first layer comprises the metal-organophosphorus complex and a substantial part of the second layer comprises the first cycloalkyl alcohol and the cycloalkyl aldehydes; and
   (iii) separating the first layer from the second layer.

2. The hydroformylation process as claimed in claim 1, wherein the cyclic olefin comprises dicyclopentadiene, tricyclopentadiene, dicyclohexadiene, 1,2,3,6-tetrahydrobenzaldehyde or cyclohexene.

3. The hydroformylation process as claimed in claim 1, wherein the pressure of hydrogen and carbon monoxide is from 0.5 MPa to 15 MPa.

4. The hydroformylation process as claimed in claim 1, further comprising preheating the metal-organophosphorus complex at 40° C. to 160° C.

5. The hydroformylation process as claimed in claim 1, further comprising hydrogenating the second layer, whereby the cycloalkyl aldehydes in the second layer are hydrogenated to form a second cycloalkyl alcohol.

6. The hydroformylation process as claimed in claim 5, wherein the step of hydrogenating the second layer is carried out at 40° C. to 160° C.

7. The hydroformylation process as claimed in claim 5, wherein the first cycloalkyl alcohol and the second cycloalkyl alcohol have the same chemical formula.

8. The hydroformylation process as claimed in claim 1, wherein the metal in the metal-organophosphorus complex is rhodium.

9. The hydroformylation process as claimed in claim 8, wherein the cyclic olefin comprises dicyclopentadiene, tricyclopentadiene, dicyclohexadiene, 1,2,3,6-tetrahydrobenzaldehyde or cyclohexene.

10. The hydroformylation process as claimed in claim 8, wherein the pressure of hydrogen and carbon monoxide is from 0.5 MPa to 15 MPa.

11. The hydroformylation process as claimed in claim 8, further comprising preheating the metal-organophosphorus complex at 40° C. to 160° C.

12. The hydroformylation process as claimed in claim 8, further comprising hydrogenating the second layer, whereby the cycloalkyl aldehydes in the second layer are hydrogenated to form a second cycloalkyl alcohol.

13. The hydroformylation process as claimed in claim 12, wherein the step of hydrogenating the second layer is carried out at 40° C. to 160° C.

14. The hydroformylation process as claimed in claim 12, wherein the first cycloalkyl alcohol and the second cycloalkyl alcohol have the same chemical formula.

* * * * *